United States Patent
Grunenberg et al.

(10) Patent No.: US 6,362,214 B1
(45) Date of Patent: Mar. 26, 2002

(54) THERMODYNAMICALLY STABLE FORM OF (R)-3-[[(4-FLUOROPHENYL) SULPHONYL]AMINO]-1,2,3,4-TETRAHYDRO-9H-CARBAZOLE-9-PROPANOIC ACID (RAMATROBAN)

(75) Inventors: Alfons Grunenberg, Dormagen; Karl-Heinz Wahl, Odenthal; Klaus-Peter Voges, Wuppertal, all of (DE)

(73) Assignee: Bayer Yakuhin, Ltd., Osaka (JP)

( * ) Notice: Subject to any disclaimer, the term of this patent is extended or adjusted under 35 U.S.C. 154(b) by 0 days.

(21) Appl. No.: 09/582,250

(22) PCT Filed: Dec. 24, 1998

(86) PCT No.: PCT/JP98/05844
§ 371 Date: Jun. 22, 2000
§ 102(e) Date: Jun. 22, 2000

(87) PCT Pub. No.: WO99/33803
PCT Pub. Date: Jul. 8, 1999

(30) Foreign Application Priority Data

Dec. 24, 1997 (DE) .......................... 197 57 983

(51) Int. Cl.[7] ..................... A61K 31/403; C07D 209/88

(52) U.S. Cl. ...................................... 514/411; 548/449

(58) Field of Search .................... 548/449; 514/411

(56) References Cited

U.S. PATENT DOCUMENTS

| | | | |
|---|---|---|---|
| 4,827,032 A | 5/1989 | Böshagen et al. | 564/90 |
| 5,684,158 A | 11/1997 | Samaan et al. | 548/449 |

FOREIGN PATENT DOCUMENTS

| | | |
|---|---|---|
| CN | 87100773 | 2/1987 |
| EP | 0242518 | 10/1987 |
| EP | 0728743 | 8/1996 |

OTHER PUBLICATIONS

L. Kofler, A. Kofler, M. Brandstätter, Thermo–Mikromethoden zur Kennzeichnung organischer Stoffe und Stoffgemische, Verlag Chemie GmbH, 1954, Weinheim/Bergstrasse, pp. 111–201.

A. Grunenberg, Polymorphie und Thermische Analyse, Pharmazie in unserer Zeit 26 (1997) 224–231.

U. Rosentreter, H. Böshagen, F. Seuter, E. Perzborn, V. B. Fiedler, "Sysnthesis and Absolute Configuration of the New Thromboxane Antagonist (3R)–3–(4–fluorophenylsulfonamido)–1,2,3, 4–tetrahydro–9–carbazolepropanoic Acid and Comparison with its Enantiomer", Arznei.–Forsch./Drug Res., 39(II): 1519–1521 (1989).

OECD–Guidelines for Testing Chemicals, Section 1, Physical–chemical Properties. Water solubility, Method No. 105, Paris 1981.

A. Burger, R. Ramberger, "On the Polymorphism of Pharmaceuticals and Other Molecular Crystals", Mikrochim. Acta 1979 II, 259–271, 273–316.

A. Grunenberg, J.–O. Henck, H. W. Siesler, "Theoretical Derivation and Practical Application of Energy/temperature diagrams as an Instrument in Preformulation Studies of Polymorphic Drug Substances", Int. J. Pharm., 128: 147–158 (1996).

*Primary Examiner*—Fiona T. Powers
(74) *Attorney, Agent, or Firm*—Jerrie L. Chiu (57) ABSTRACT

The present invention relates to a thermodynamically stable modification of the active compound ramatroban of formula (I). The thermodynamically stable form is prepared either by melting of the metastable form and subsequent recrystallization or by seeding a solution of the metastable active compound with a seed crystal of the thermodynamically stable form. The thermodynamically stable active compound can be employed as an asthma agent.

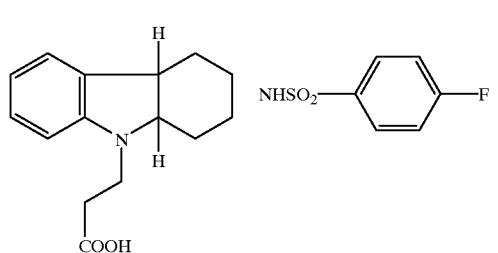

(I)

6 Claims, 6 Drawing Sheets

DSC thermogram of ramatroban

THERMODYNAMICALLY STABLE FORM OF (R)-3-[[(4-FLUOROPHENYL)SULPHONYL]AMINO]-1,2,3,4-TETRAHYDRO-9H-CARBAZOLE-9-PROPANOIC ACID (RAMATROBAN)

The invention relates to a new form of ramatroban which is thermodynamically stable at room temperature, a process for its preparation, pharmaceuticals comprising this form, and their use in the control of diseases.

The preparation and use of ramatroban as a thromboxane A2 antagonist has already been disclosed in EP 242 518. U.S. Pat. No. 4,827,032, which is hereby incorporated by reference herein.

Figure 1:
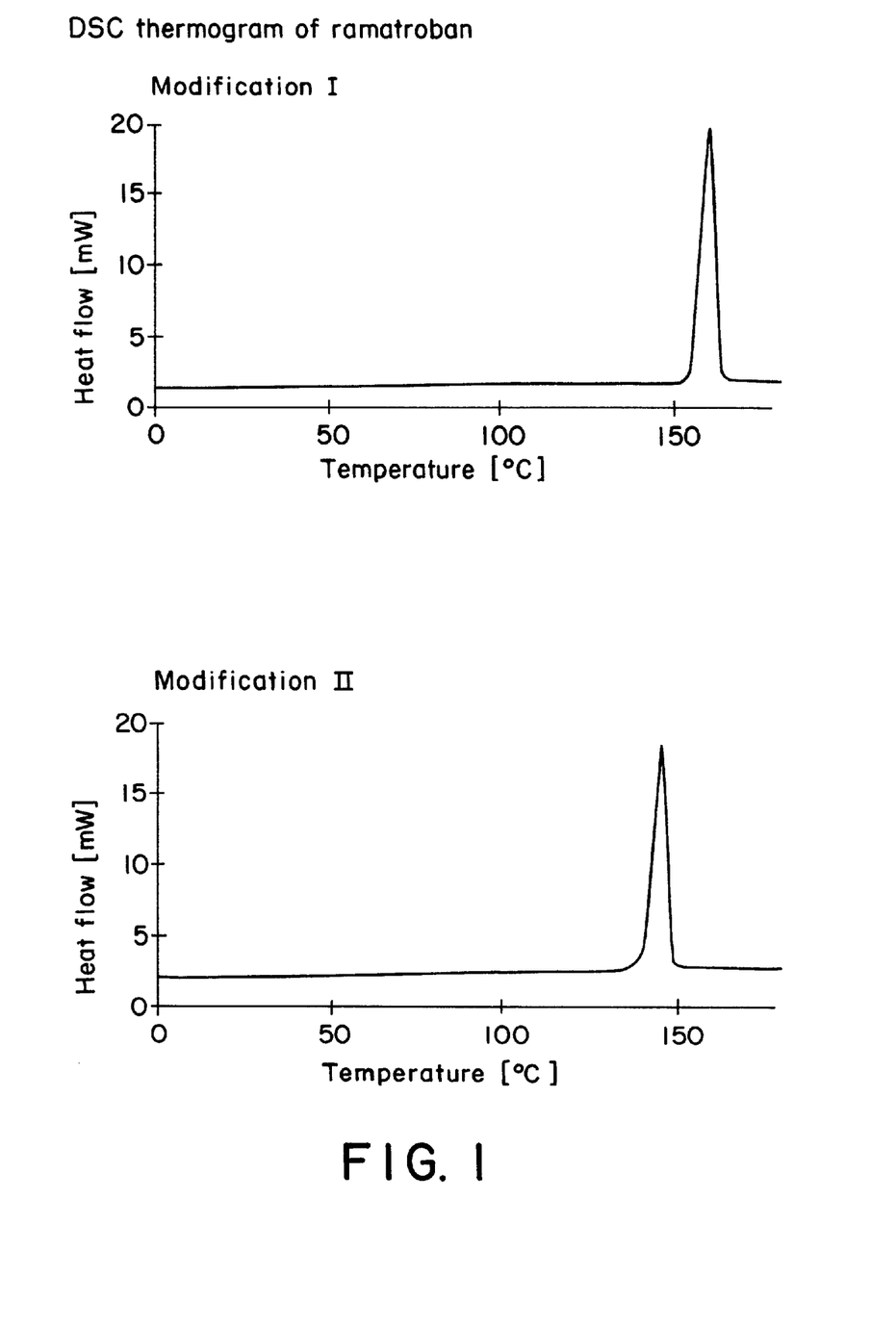
Figure 2:
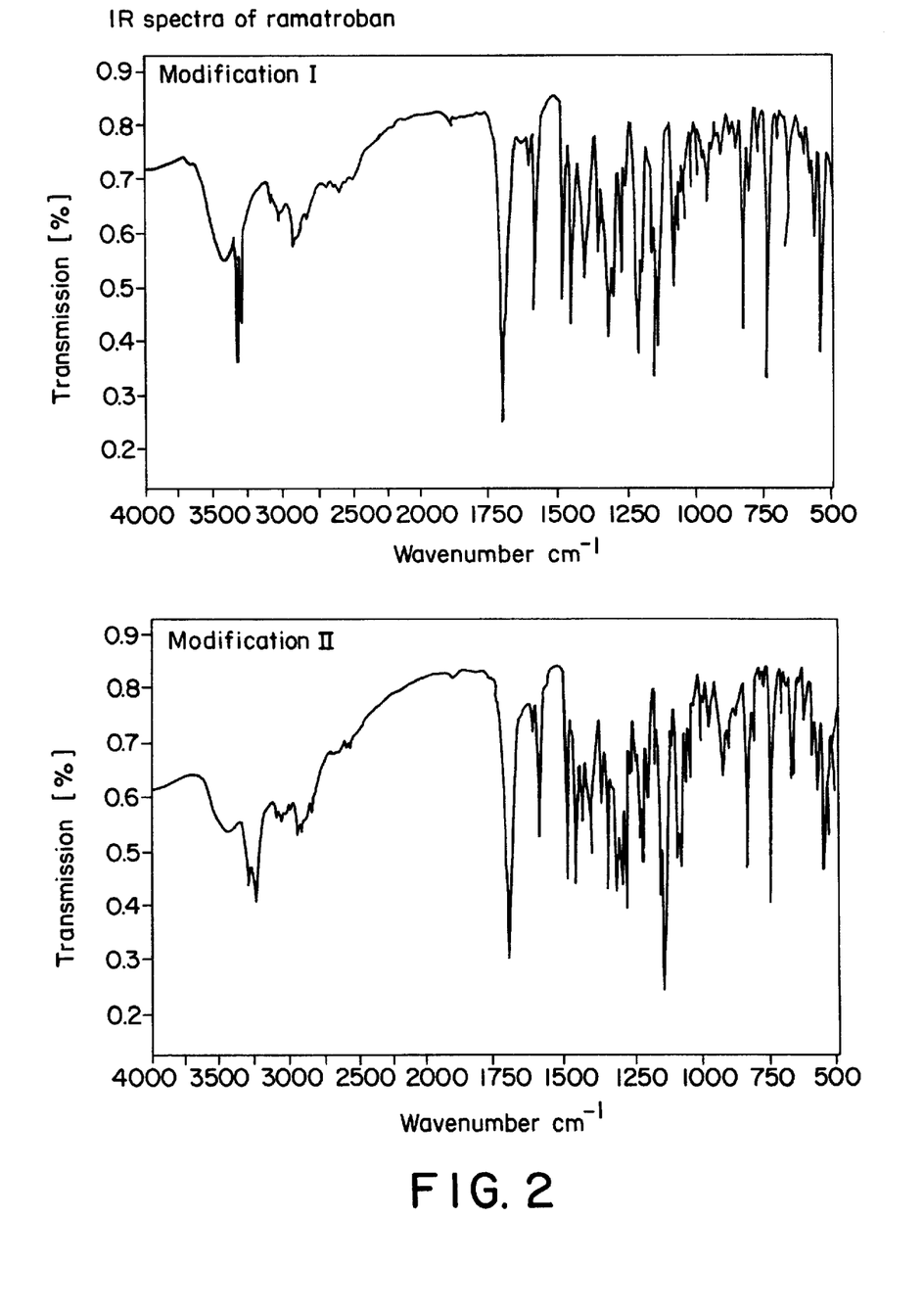
Figure 3:
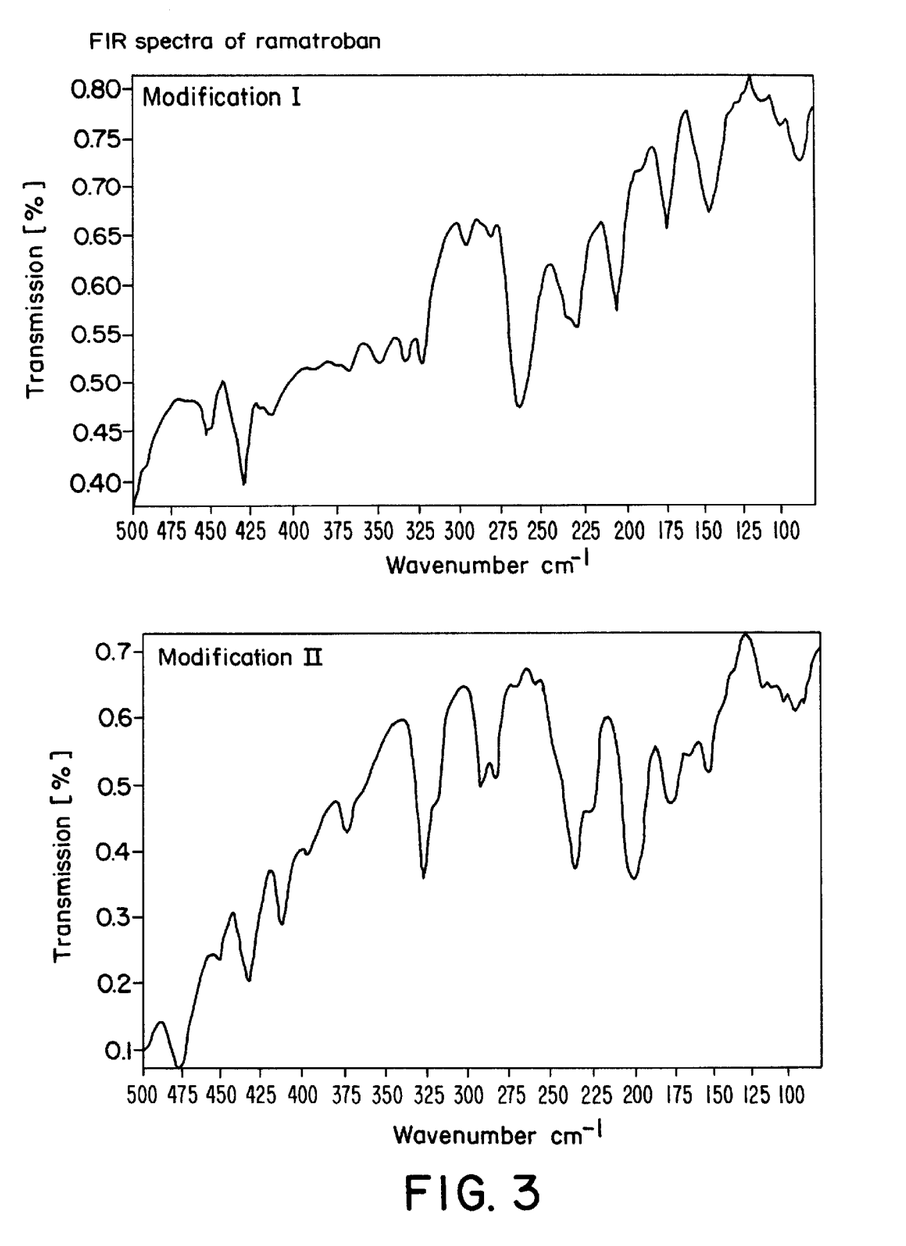
Figure 4:
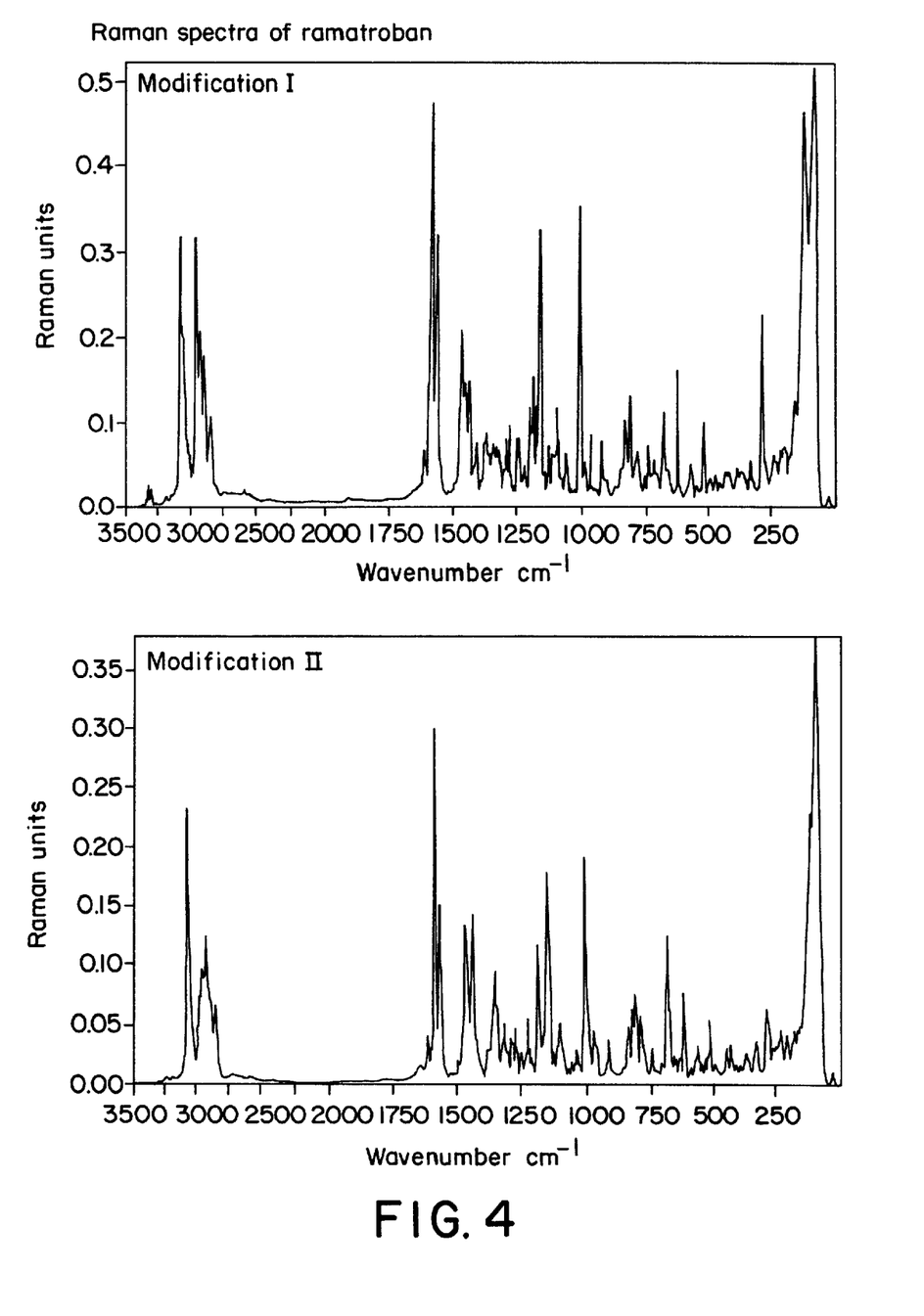
Figure 5:
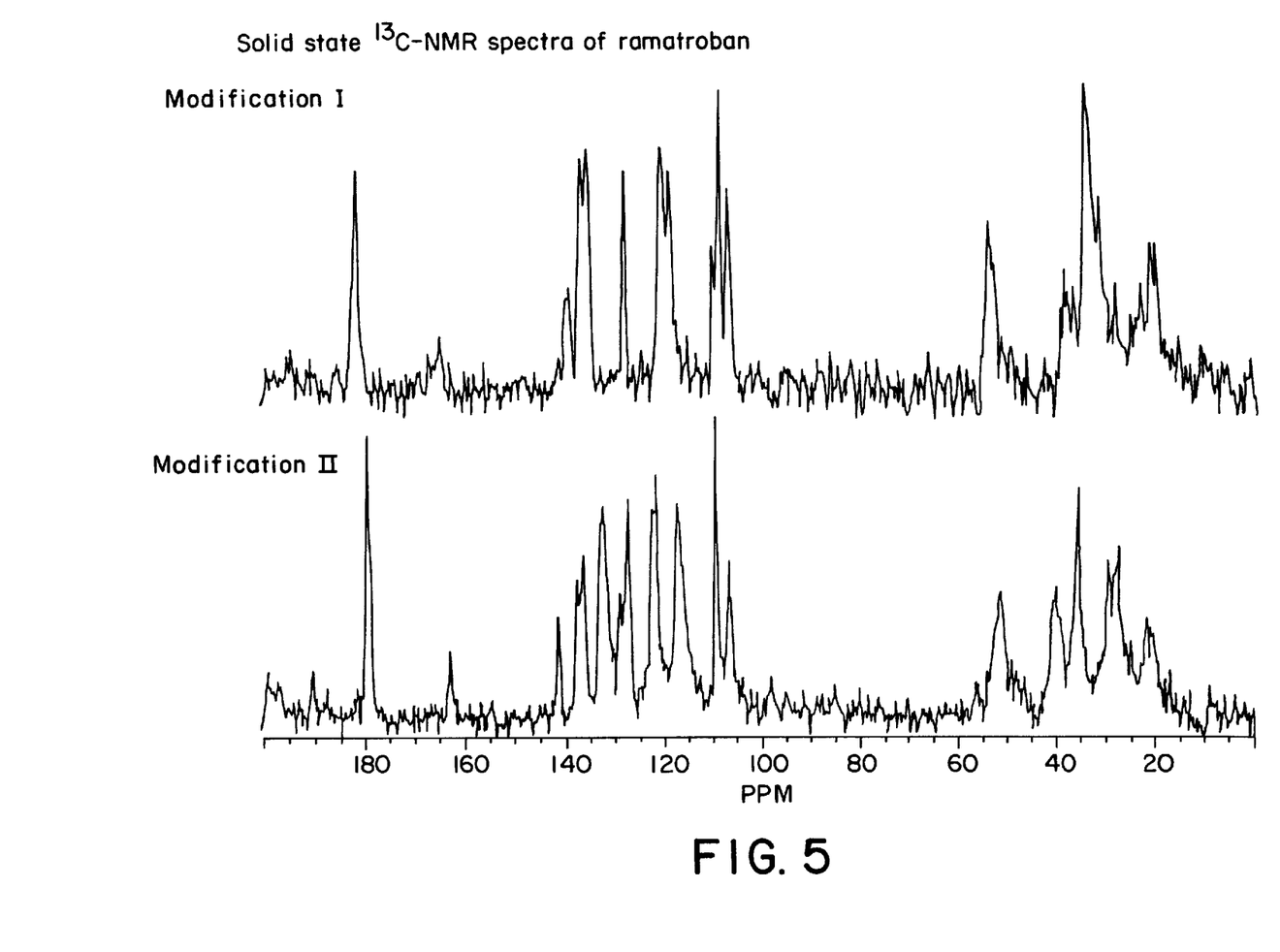
Figure 6:
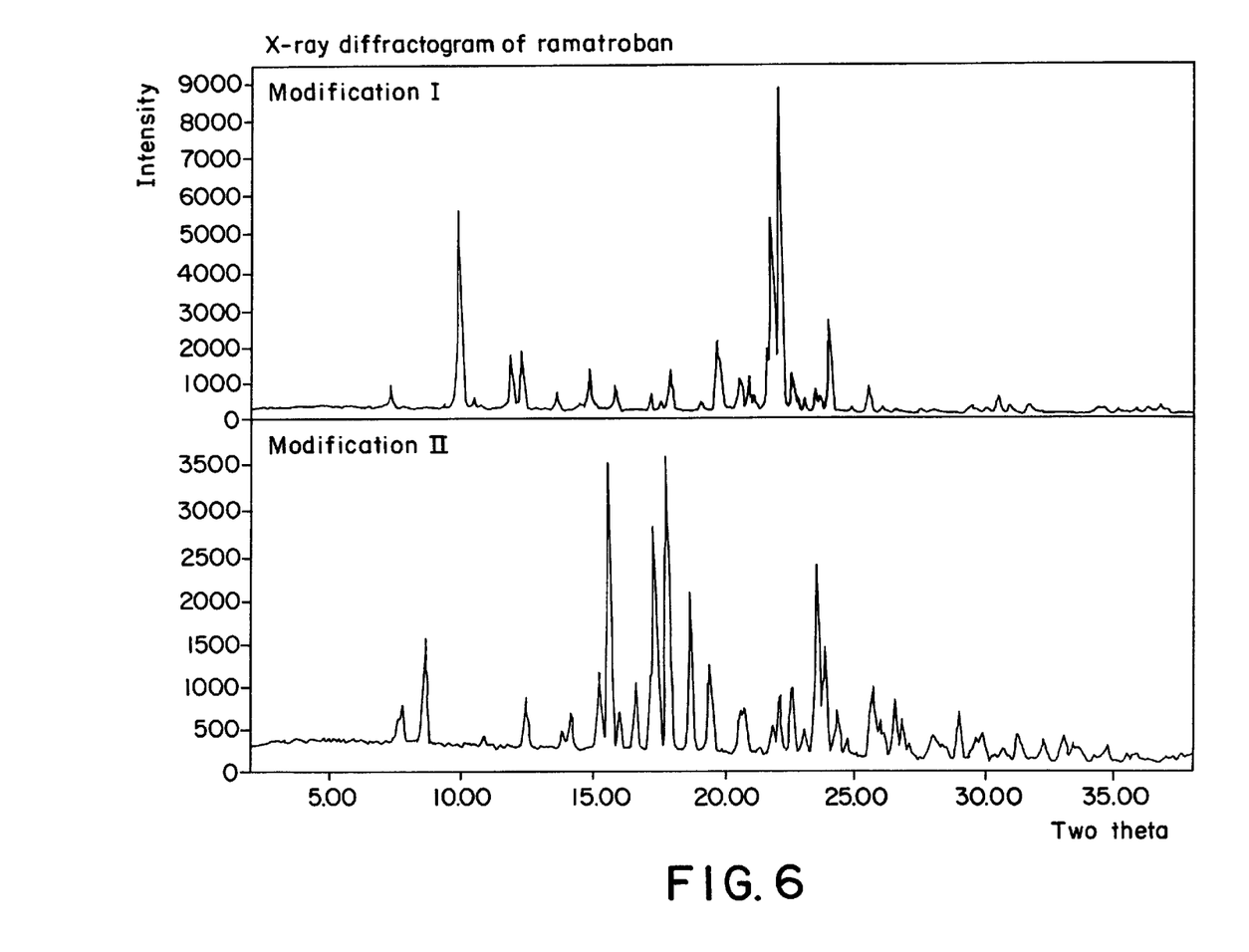

In the manner described there, ramatroban is obtained in the form of a crystal modification which is designated in the following text as modification II. Mod. II has a melting point of 137° C. and a malt enthalpy of 80 J/g (DSC, heating rate 2 K min$^{-1}$) and a characteristic X-ray diffractogram, IR spectrum, $^{13}$C-solid state NMR spectrum, FIR spectrum, Raman spectrum (FIGS. 1–6). It has now been found that Mod. II is metastable and therefore is not suitable for use in pharmaceutical formulations, such as, for example, solid and semi-solid preparations.

Surprisingly, a second modification of ramatroban has now been found which is thermodynamically stable and is also stable on storage after processing by means of suspensions and is therefore particularly suitable for use in pharmaceutical formulations, such as, for example, suspensions or creams, but also in other preparations which are prepared by means of suspended active compound, such as, for example, in aqueous granulation or wet-grinding. This new modification is designated in the following text as modification I. The present invention also relates to pharmaceutical formulations which contain ramatroban in the modification I as active substance. The formulation can contain one or more pharmaceutically acceptable auxiliaries, such as, for example, binders, solvents, fillers, etc.

J. Halbelian, W. McCrowne, J. Pharm. Sci. 58 (1969) 911, and J.-O. Henck et al., Pharm. Ind. 59 (1997) 165–169 disclose that when using a thermodynamically metastable polymorphic form in solid and semi-solid formulations, such as, for example, tablets, suspensions and ointments, the stable form can result. As an attendant phenomenon here, undesired crystal growth, changes in the bioavailability, caking, etc. are observed. The two crystal modifications of ramatroban differ in their solubility at-room temperature by 60%. By means of the use according to the invention of the stable modification I, it is ensured that no change in solubility can occur as a result of conversion. This increases the safety of preparations of ramatroban and the risk for the patients is thus reduced.

In comparison with Mod. II, Mod. I has a clearly distinguishable DSC thermogram, X-ray diffractogram, $^{13}$C-solid state NMR spectrum, FIR spectrum and Raman spectrum (FIGS. 1–6). The melting point of Mod. I is 151° C. and the melt enthalpy is 87 J/g.

The DSC and TGA thermograms were obtained using a DSC 7 and TGA 7 from Perkin-Elmer. The X-ray diffractograms were recorded in a Stoe transmission diffractometer. The IR, FIR and Raman spectra were recorded using Fourier IR spectrometers IFS 66 (IR), IFS 66v (FIR) and IFS 88 (Raman) from Bruker. The $^{13}$C-solid state NMR spectra were recorded using a Bruker MSL 300.

The crystal modification of ramatroban is employed in high purity in pharmaceutical formulations. For reasons of stability, Mod. I should not contain relatively large proportions of Mod. II. A grade of active compound with less than 10% of Mod. II, very particularly preferably with less than 5%, is preferred.

Mod. I is prepared by suspending ramatroban of modification II in water or inert substances, e.g. in lower alcohols, ketones or alkanes, seeding with crystals of Modification I and stirring until the desired degree of conversion is achieved, particularly preferably until quantitative conversion to Mod. I. As a rule, this conversion takes place at 20–50° C., preferably at 40° C. The crystals of Mod. I obtained are separated off and, to remove solvent present, dried to constant weight at room temperature in vacuo or at elevated temperature.

To prepare the seed crystals needed, the active compound is thoroughly melted and then rapidly cooled to room temperature. The amorphous form of the active compound thus obtained is suspended in an inert solvent at room temperature and stirred until it is completely converted into the thermodynamically stable crystal modification. The residue is filtered and dried to constant mass in vacuo.

EXAMPLES

Example 1
Preparation of Seed Crystals from the Melt

About 300 mg of ramatroban of Mod. II are thoroughly melted and rapidly cooled to room temperature. The amorphous substance is suspended in 5 ml of ethanol/water (1:1) and the suspension is stirred at room temperature for 24 h. After the end of the stirring time, the suspension is filtered and the residue is dried in vacuo at room temperature.

Example 2
Seeding Process 130 g of ramatroban (Modification II) are dissolved in 650 g of n-butyl acetate and 15 g of water at about 40° C. 175 g of solvent are distilled off in vacuo at 40–45° C. The solution is then seeded with 1 g of ramatroban (Modification I) and a further 300 g of solvent are distilled off in vacuo at 40 to 45° C. The crystal suspension obtained is cooled to room temperature and stirred for a few hours. It is filtered off with suction, washed with n-butyl acetate and methyl tert-butyl ether and dried in vacuo at 50° C. About 100 g of ramatroban are obtained (Modification I).

Example 3
Precipitation Method 75 g of ramatroban (Modification II) are dissolved in 135 g of ethyl acetate with warming. 85 g of petroleum ether (35/60) are added dropwise at about 40° C. and the batch is seeded with 1 g of ramatroban (Modification I). The mixture is stirred at 40° C. for about 2–3 hours and then cooled to room temperature. A further 130 g of petroleum ether (35/60) are added to the suspension and it is additionally stirred at room temperature for about 5 hours. It is filtered off with suction, washed with 100 g of petroleum ether (35/60) and dried at 50° C. in vacuo. About 65 g of ramatroban (Modication I) are obtained.

Example 4
Conversion in Suspension 1

50 g of ramatroban (Modification II) are suspended in 75 g of n-butyl acetate and mixed with 0.5 g of ramatroban (Modification I). The mixture is stirred at room temperature for about 100 hours. It is then filtered off with suction, washed with methyl tert-butyl ether and dried at 50° C. in vacuo. About 40 g of ramatroban (Modification I) are obtained,

Example 5
Conversion in Suspension 2

About 0.5 g of Mod. I and II (mixing ratio about 1:1) are suspended in 8 ml of n-heptane and refluxed at about 80° C. After one week, the suspension is filtered and the residue is dried in vacuo at room temperature for one day.

Example 6
Production of Tablets 4590 g of microfine ramatroban of Mod. I are dispersed in a homogenizer with 9180 g of an aqueous HPC-L (367 g) and then filtered through a sieve having a 355 im mesh width. The granulation liquid is reacted in a granulator with 13,500 g of a premixed and preheated aqueous solution, consisting of 3162 g of lactose, 4860 g of HPC-L and 540 g of HPC-M, to form granules. The resulting granules are dried at 65° C. Pressing is then carried out in a rotary press to give tablets having a diameter of 9.0 mm.

TABLE 1

Differential Scanning Calorimetry

|  | Mod. I | Mod. II |
|---|---|---|
| Melting point | 151 | 137 |
| Melt enthalpy | 87 | 80 |

TABLE 2

X-ray diffractometry

Peak maxima [2 theta]

| Mod. I | Mod. II |
|---|---|
| 7.5 | 7.8 |
| 9.4 | 8.7 |
| 10.1 | 10.9 |
| 10.6 | 12.5 |
| 12.0 | 13.8 |
| 12.4 | 14.1 |
| 13.7 | 15.3 |
| 14.6 | 15.6 |
| 15.0 | 16.0 |
| 16.0 | 16.6 |
| 17.3 | 17.2 |
| 17.7 | 17.3 |
| 18.0 | 17.8 |
| 19.2 | 18.7 |
| 19.8 | 19.4 |
| 20.3 | 20.5 |
| 20.7 | 20.7 |
| 21.0 | 21.3 |
| 21.2 | 21.8 |
| 21.7 | 22.1 |
| 21.9 | 22.6 |
| 22.2 | 23.0 |
| 22.7 | 23.6 |
| 22.9 | 23.8 |
| 23.1 | 24.3 |
| 23.6 | 24.7 |
| 23.7 | 25.7 |
| 24.1 | 25.9 |
| 24.9 | 26.1 |
| 25.6 | 26.5 |
| 26.2 | 26.8 |
| 26.6 | 27.1 |
| 27.5 | 28.0 |
| 28.0 | 28.4 |
| 29.5 | 29.0 |
| 30.0 | 29.6 |
| 30.1 | 29.9 |
| 30.5 | 30.4 |
| 31.0 | 30.7 |
| 31.7 | 31.2 |
| 32.2 | 32.2 |
| 32.6 | 33.0 |
| 32.8 | 33.4 |
| 34.4 | 33.6 |
| 34.6 | 34.3 |
| 35.1 | 34.7 |
| 35.5 | 35.5 |
| 35.8 | 35.7 |
| 36.2 | 35.9 |
| 36.7 | 36.9 |
| 36.9 | 37.2 |
| 37.0 | 37.5 |
| 37.4 |  |
| 37.7 |  |

TABLE 3

IR spectroscopy

Peak maxima [cm$^{-1}$]

| Mod. I | Mod. II |
|---|---|
| 3338 | 3298 |
| 3316 | 3244 |
| 3053 | 2943 |
| 2944 | 1697 |
| 1708 | 1615 |
| 1614 | 1591 |
| 1592 | 1495 |
| 1496 | 1466 |
| 1470 | 1447 |
| 1431 | 1416 |
| 1378 | 1379 |
| 1335 | 1357 |
| 1318 | 1327 |
| 1294 | 1305 |
| 1227 | 1292 |
| 1179 | 1274 |
| 1167 | 1240 |
| 1156 | 1228 |
| 1097 | 1213 |
| 1079 | 1186 |
| 1067 | 1164 |
| 1055 | 1151 |
| 1032 | 1103 |
| 1013 | 1088 |
| 972 | 1068 |
| 922 | 1055 |
| 868 | 1013 |
| 836 | 980 |
| 817 | 931 |
| 782 | 841 |
| 746 | 817 |
| 708 | 782 |
| 671 | 751 |
| 615 | 710 |
| 577 | 674 |
| 550 | 665 |
| 542 | 626 |
| 520 | 590 |
|  | 575 |
|  | 556 |
|  | 538 |
|  | 520 |

TABLE 4

13C-Solid state NMR spectroscopy

Peak maxima [ppm]

| Mod. I | Mod. II |
|---|---|
| 181.1 | 179.2 |
| 164.0 | 163.0 |
| 139.4 | 141.5 |
| 138.8 | 137.6 |
| 136.2 | 136.4 |
| 135.0 | 132.5 |
| 127.7 | 129.0 |
| 120.0 | 128.4 |
| 118.2 | 127.5 |
| 117.0 | 122.6 |
| 109.3 | 121.7 |
| 107.9 | 117.2 |
| 106.2 | 115.7 |
| 54.0 | 109.2 |
| 53.2 | 106.6 |
| 52.1 | 51.6 |
| 50.6 | 40.1 |
| 38.8 | 37.5 |
| 38.1 | 35.9 |
| 37.1 | 34.8 |
| 36.1 | 29.8 |
| 35.3 | 27.8 |
| 33.9 | 26.4 |
| 32.3 | 25.5 |
| 31.4 | 22.2 |
| 29.6 | 21.7 |
| 29.0 | 21.3 |
| 27.7 | |
| 24.9 | |
| 24.1 | |
| 23.1 | |
| 20.8 | |
| 19.8 | |

TABLE 5

FIR spectroscopy

Peak maxima [cm$^{-1}$]

| Mod. I | Mod. II |
|---|---|
| 452 | 498 |
| 429 | 477 |
| 413 | 449 |
| 388 | 432 |
| 368 | 411 |
| 350 | 395 |
| 334 | 373 |
| 324 | 326 |
| 297 | 291 |
| 282 | 281 |
| 264 | 235 |
| 231 | 201 |
| 207 | 177 |
| 176 | 152 |
| 148 | 116 |
| 115 | 101 |
| 101 | 94 |
| 88 | 88 |

TABLE 6

Raman spectroscopy

Peak maxima [cm$^{-1}$]

| Mod. I | Mod. II |
|---|---|
| 3080 | 3070 |
| 3069 | 3046 |
| 3056 | 2960 |
| 2955 | 2925 |
| 2925 | 2850 |
| 2898 | 1615 |
| 2851 | 1589 |
| 1613 | 1570 |
| 1580 | 1467 |
| 1566 | 1443 |
| 1471 | 1354 |
| 1438 | 1315 |
| 1412 | 1290 |
| 1369 | 1273 |
| 1293 | 1228 |
| 1277 | 1186 |
| 1236 | 1150 |
| 1180 | 1100 |
| 1165 | 1014 |
| 1155 | 981 |
| 1123 | 921 |
| 1091 | 847 |
| 1059 | 817 |
| 1012 | 794 |
| 973 | 693 |
| 928 | 628 |
| 833 | 567 |
| 817 | 520 |
| 785 | 435 |
| 743 | 330 |
| 682 | 287 |
| 629 | 227 |
| 574 | 91 |
| 521 | |
| 334 | |
| 283 | |
| 199 | |
| 122 | |
| 90 | |
| 82 | |

What is claimed is:

1. Thermodynamically stable Modification I of ramatroban, comprising a characteristic selected from the group consisting of:
    (a) a melting point of 151° C. (DSC, 2 Kmin$^{-1}$);
    (b) an X-ray diffractogram having reflections at 10.1, 12.0 and 19.8 (2 theta);
    (c) an IR spectrum having peak maxima at 3338 cm$^{-1}$, 1708 cm$^{-1}$ and 1431 cm$^{-1}$;
    (d) a $^{13}$C-solid state NMR spectrum having peak maxima at 107.9 ppm, 118.2 ppm and 135.0 ppm;
    (e) an FIR spectrum having peak maxima at 264 cm$^{-1}$ and 207 cm$^{-1}$; and
    (f) a Raman spectrum having peak maxima at 3080 cm$^{-1}$, 1580 cm$^{-1}$ and 122 cm$^{-1}$.

2. Process for the preparation of seed crystals of the thermodynamically stable Modification I of ramatroban according to claim 1, characterized in that the active compound is converted into the amorphous form by melting and rapid cooling and this is then converted into the stable Modification I by stirring in inert solvents.

3. Process for the preparation of a thermodynamically stable form of ramatroban according to claim 1, characterized in that a thermodynamically metastable modification of ramatroban is suspended in water or inert organic solvents, seeded with the stable Modification I and the conversion is carried out until the desired degree of conversion is achieved.

4. Pharmaceutical composition comprising a thermodynamically stable form of ramatroban according to claim 1.

5. A method of treating a thromboxane A2 mediated disease or condition, comprising administering to a patient in need thereof the thermodynamically stable Modification I of ramatroban according to claim 1.

6. The method of claim 5, wherein said thromboxane A2 mediated disease or condition is selected from the group consisting of thromboses, thromboembolisms, ischaemias, asthma and allergic reactions.

* * * * *